(12) United States Patent
Falkner et al.

(10) Patent No.: US 8,486,089 B2
(45) Date of Patent: Jul. 16, 2013

(54) INTRODUCER FOR LEAD DELIVERY

(75) Inventors: Phillip C. Falkner, Minneapolis, MN (US); Eric H. Bonde, Minnetonka, MN (US); Dale F. Seeley, Spring Park, MN (US); Patrick P. Senarith, Circle Pines, MN (US); Steven L. Waldhauser, White Bear Township, MN (US); Kendra Yasger, Big Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 455 days.

(21) Appl. No.: 12/706,225

(22) Filed: Feb. 16, 2010

(65) Prior Publication Data

US 2011/0202067 A1    Aug. 18, 2011

(51) Int. Cl.
*A61B 19/00* (2006.01)
(52) U.S. Cl.
USPC .......................... 606/129; 607/116; 607/117
(58) Field of Classification Search
USPC ....... 606/129, 1, 86 A; 607/116, 117; 604/19, 604/95.01, 523; 600/201–219
See application file for complete search history.

(56) References Cited

U.S. PATENT DOCUMENTS

| | | | |
|---|---|---|---|
| 4,406,656 A * | 9/1983 | Hattler et al. | 604/523 |
| 4,738,666 A | 4/1988 | Fuqua | |
| 5,431,168 A | 7/1995 | Webster | |
| 5,868,717 A | 2/1999 | Prosl | |
| 6,059,739 A | 5/2000 | Baumann | |
| 6,697,677 B2 | 2/2004 | Dahl | |
| 6,836,687 B2 | 12/2004 | Kelley | |
| 7,037,290 B2 | 5/2006 | Gardeski | |
| 7,184,828 B2 | 2/2007 | Hill | |
| 7,473,239 B2 | 1/2009 | Wang | |
| 2005/0107861 A1 * | 5/2005 | Harris et al. | 607/116 |
| 2005/0288759 A1 * | 12/2005 | Jones et al. | 607/116 |
| 2006/0235458 A1 * | 10/2006 | Belson | 606/191 |
| 2008/0015625 A1 | 1/2008 | Ventura | |
| 2009/0270960 A1 | 10/2009 | Zhao | |
| 2010/0185083 A1 * | 7/2010 | Neidert et al. | 600/424 |

\* cited by examiner

*Primary Examiner* — Gary Jackson
*Assistant Examiner* — Katrina Stransky
(74) *Attorney, Agent, or Firm* — Mueting Raasch & Gebhardt PA

(57) ABSTRACT

Devices and methods for implanting leads along a spinal cord include an introducer having a main body defining a lumen and one or more collapsible and expandable side sheaths attached to the main body. The side sheaths may be collapsed as the introducer is positioned in a desired location of a patient to maintain a low profile. Once the introducer is placed, the side sheaths may be expanded to receive a lead. A lead may also be inserted through a lumen of the main body. Once the leads are inserted, the introducer may be withdrawn over the leads, leaving the leads implanted in the desired region in a desired orientation.

12 Claims, 16 Drawing Sheets

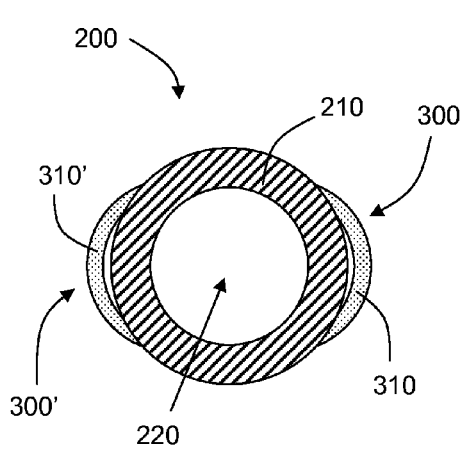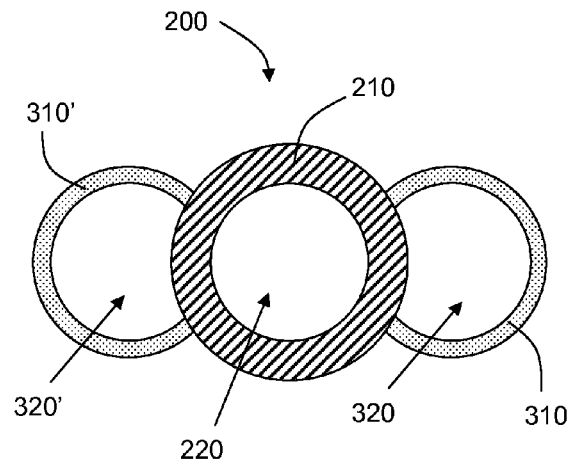
FIG. 7A    FIG. 7B
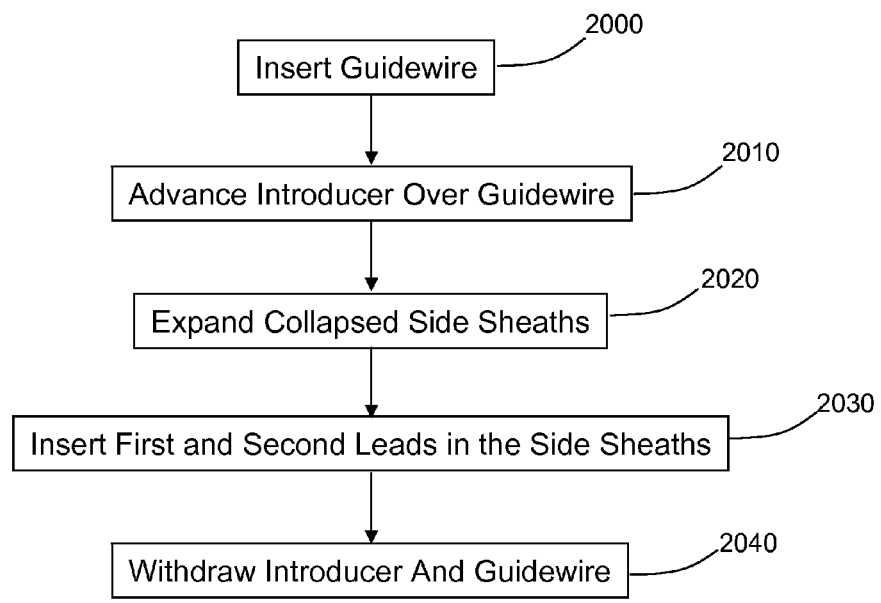
FIG. 8

INTRODUCER FOR LEAD DELIVERY

FIELD

The present disclosure relates generally to devices and methods for implanting medical leads; particularly for epidural placement of medical leads.

BACKGROUND

Spinal cord stimulation (SCS) involves application of electrical signals to the spinal cord at specifically targeted locations, typically via leads and electrodes that are either surgically implanted post laminectomy, or inserted percutaneously. Delivering stimulation to the appropriate location on the spinal cord causes paresthesia that overlays the pain region to reduce the area of perceived pain. SCS can result in the patient experiencing paresthesia in a relatively large area, including more than one limb.

With SCS, leads are typically placed epidurally such that electrodes are positioned along the dorsal horn of the spinal cord. Typically two leads are employed, where each lead is placed on either side of the midline. It is often desirable for the leads to be placed parallel to one another. However, proper positioning of the leads takes a great deal of skill and can be difficult to achieve due to the delicacy and anatomical considerations of the epidural region.

BRIEF SUMMARY

The present disclosure describes, among other things, devices and methods that allow for epidural placement of two parallel leads on either side of the midline of the spinal cord.

In various embodiments, a method for implanting first and second leads along a spinal cord of a patient is described. The method includes inserting an introducer in proximity to the patient's spinal cord, wherein the introducer has a first lumen and a second lumen. The second lumen has a collapsed configuration and an expanded configuration. The second lumen is in the collapsed configuration as the introducer is inserted. The method further includes inserting the first lead into the first lumen of the introducer; expanding the second lumen to the expanded configuration and inserting the second lead into the expanded second lumen. The method also includes withdrawing the introducer and leaving the first and second leads implanted along the spinal cord.

In various embodiments, a method for implanting a first and second lead parallel to each other and parallel to the midline of a patient's spinal cord is described. The method includes inserting an introducer in proximity to the patient's spinal cord. The introducer has a first lumen and a second lumen. The second lumen is collapsible and expandable and is collapsed as the introducer is inserted. The introducer is inserted such that a distal portion of the first lumen is parallel to the midline of the spinal cord. The method further includes expanding the second lumen such that a distal portion of the lumen resides on an opposing side of the midline relative to the first lumen. The method also includes inserting the first lead into the first lumen of the introducer; inserting the second lead into the second lumen; withdrawing the introducer and leaving distal portions of the first and second leads parallel to each other and parallel to the midline of a patient's spinal cord.

In various embodiments, an alternative method for implanting a first and second lead parallel to each other and parallel to the midline of a patient's spinal cord is described. The method includes inserting an introducer in proximity to the patient's spinal cord. The introducer has a main body defining a main lumen, a first side sheath defining a first side lumen, and a second side sheath defining a second side lumen. The first and second side sheaths are attached to generally opposing sides of the main body and are collapsible and expandable and are collapsed as the introducer is inserted. The introducer is inserted such that a distal portion of the main lumen is parallel to the midline of the spinal cord. The method further includes expanding the first side sheath such that a distal portion of the first lumen resides on a side of the midline of the patient's spinal cord and inserting the first lead into the first side lumen. The method also includes expanding the second side sheath such that a distal portion of the second side lumen resides on a side of the midline of the patient's spinal cord opposing the side that the first side lumen resides and inserting the second lead into the second side lumen. The method additionally includes withdrawing the introducer and leaving distal portions of the first and second leads parallel to each other and parallel to the midline of a patient's spinal cord.

In various embodiments, a system for implanting medical leads in a patient's body is described. The system includes an introducer and needle-tipped dilator. The introducer includes a main body member having a proximal portion and a distal portion and defining a lumen extending within the main body member through the distal portion and the proximal portion. The lumen is configured to slidably receive the dilator. The introducer further includes a steering element operably coupled to the main body member and an actuation element operably coupled to the steering element. Actuation of the actuation element causes the distal portion of the main body member to deflect in a predetermined direction via movement of the steering element. The introducer also includes a first side sheath defining a first side lumen. The first side sheath is attached to the main body member and is expandable from a collapsed configuration to an expanded configuration. In the expanded configuration, the side lumen is configured to receive a medical lead. The dilator has a needle-tipped distal end configured to penetrate the skin of a patient. The introducer may also include a second side sheath defining a second side lumen. The second side sheath is attached to the main body member and is expandable from a collapsed configuration to an expanded configuration. In the expanded configuration, the second side lumen is configured to receive a medical lead. Due to the ability of the first side sheath and the second side sheath, if present, to adopt a collapsed configuration, the profile of the introducer may be kept small while the introducer is being placed. Once properly placed, the side sheaths may be expanded. Leads may then be inserted into the side lumens or the lumen of the main body. Through the use of such an introducer, the leads may be placed such that they are oriented parallel to each other.

One or more embodiments of the devices or methods described herein may provide one or more advantages relative to prior devices and methods for implanting leads epidurally along the spinal cord. For example, the methods and devices described herein provide for more ready epidural placement of leads in the proper orientation, which should provide enhanced efficacy for SCS therapies. In addition, systems including a needle-tipped dilator may allow for more efficient surgical placement of leads, eliminating some steps to an already difficult procedure. These and other aspects and advantages will be apparent to one of skill in the art from the accompanying detailed description and drawings.

BRIEF DESCRIPTION OF THE DRAWINGS

FIGS. 7A-B are schematic cross-sectional views of an embodiment of an introducer having two expandable and collapsible side lumens in a collapsed state (7A) and in an expanded state (7B).

FIG. 8 is a flow diagram of a method for implanting two leads using a device similar to the device depicted in FIGS. 7A-B.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope of spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "about" means +/−10% of the enumerated numerical value that it precedes. For example, "about" may mean +/−5%, or +/−3% of the enumerated numerical value that it precedes.

The present disclosure describes, among other things, devices and methods that allow for epidural placement of two parallel leads on either side of the midline of the spinal cord.

Figure 1:
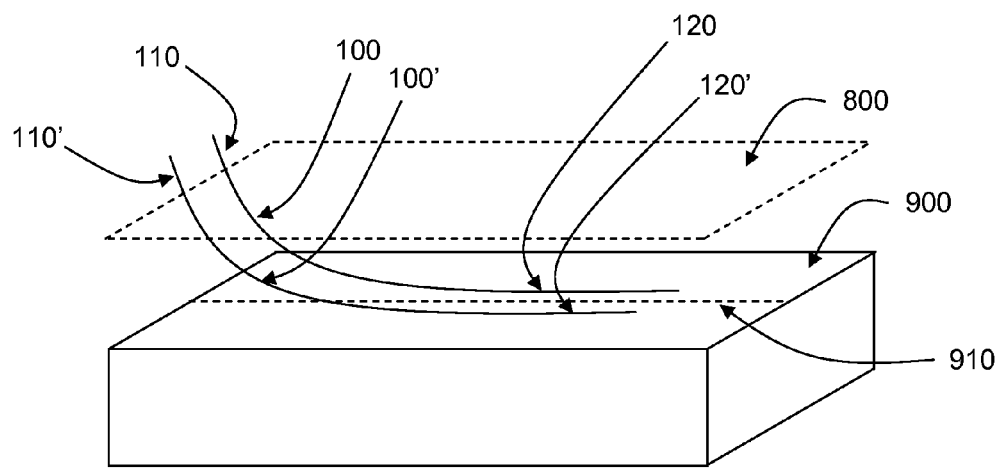
FIG. 1 is a schematic view showing two leads percutaneously inserted along a spinal cord.

Referring now to FIG. 1, a schematic view of two leads 100, 100' percutaneously inserted into a patient are shown. In the depicted embodiment, the proximal ends 110, 110' of the leads 100, 100' extend outside of the patient's skin 800. The proximal ends 110, 110' may be tunneled and connected with an implantable electrical device (not shown), such as an electrical signal generator. The distal end portions 120, 120' of the leads in the depicted embodiment are implanted parallel to each other on either side of the midline 910 of the spinal cord 900. Typically, the distal portions 120, 120' of the leads are implanted such that electrical signals may be applied to the dorsal horn or dorsal roots of the spinal cord 900.

Figure 2:
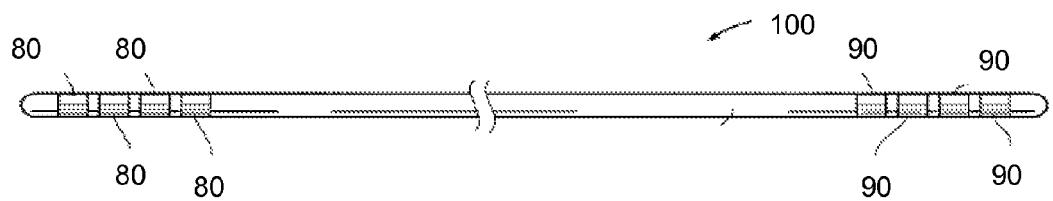
FIG. 2 is a schematic perspective view of a lead.

In FIG. 2, a schematic perspective view of a lead 100 is shown. The lead 100 includes a distal portion including one or more electrodes 90. The depicted lead 100 has four electrodes 90, but it will be understood that the lead may have any suitable number of electrodes, such as 1, 2, 3, 4, 5, 6, 7, 8, 16, or 32 electrodes. The proximal portion of the lead 100 includes one or more contacts 80. Typically, the lead 100 has an equal number of contacts 80 and electrodes 90. Each contacts 80 is then electrically coupled to a corresponding electrode 90 via a conductor (not shown) running internally within the lead 100. The contacts 80 are configured to form an electrical connection with an active electrical device (not shown) that can apply an electrical signal to the one or more contacts, which signal may be transmitted to the corresponding electrode(s), and thus delivered to target tissue of the patient (e.g., the spinal cord 900, as depicted in FIG. 1).

Figure 3:
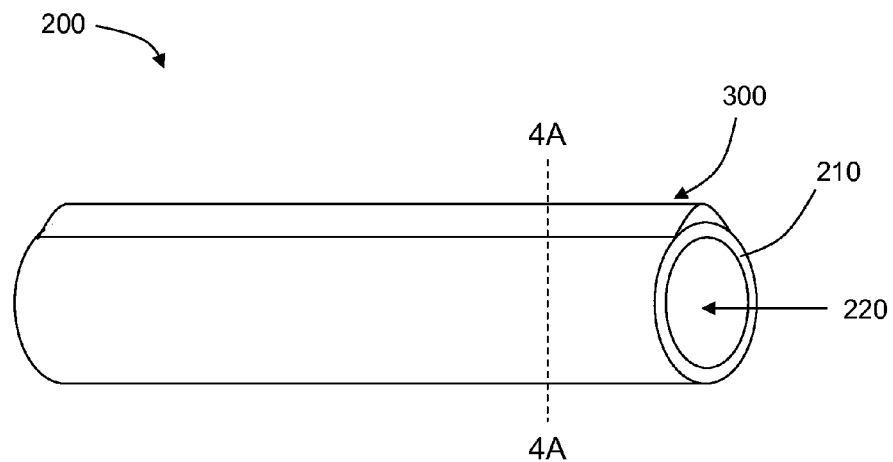
FIG. 3 is a schematic perspective view of an embodiment of an introducer having a collapsible and expandable side lumen.
Figure 4A:
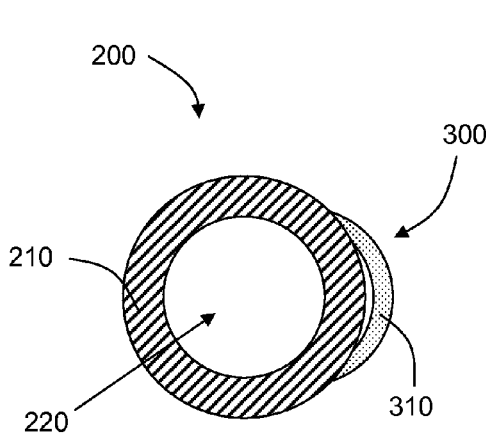
FIG. 4A is a schematic cross-sectional view of an embodiment of the introducer of FIG. 3 taken through line 4A-4A.
Figure 4B:
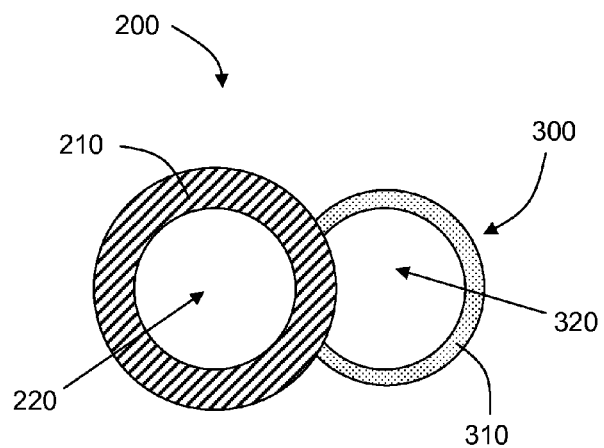
FIG. 4B is a schematic cross-sectional view of an embodiment of the introducer of FIG. 4A, where a side sheath is in an expanded configuration.

Referring now to FIGS. 3, 4A and 4B schematic views of an introducer device 200 configured to percutaneously introduce leads into a patient is shown. In the depicted embodiment, the introducer 200 includes a main body member 210 defining a lumen 220 that extends from the proximal end to the distal end of the body 210. The introducer 200 also includes an expandable and collapsible side sheath 300 configured to allow a lead to be inserted there through when in the expanded configuration. Preferably, the expanded configuration that allows insertion of a lead is an unstressed configuration. FIG. 4A, which is a schematic sectional view taken through line 4A-4A of the introducer 200 of FIG. 3, shows the side sheath 300 in a collapsed configuration, and FIG. 4B shows the side sheath 300 in an expanded configuration. The side sheath 300 has a body member 310 defining a lumen 320 running the length of the sheath 300. The side sheath 300 is attached to the main body member 210 via any suitable mechanism, such as laser welding, thermal bonding, adhesive or the like.

The main body 210 of the introducer 200 may be formed of any suitable materials and may be made in any suitable manner, such as know for fabrication of introducer sheaths as known in the art. For example, the main body member may be formed of a simple polymeric or metallic flexible tube having sufficient stiffness to be advanced in tissue of a patient. The main body member may include a reinforcement member. For example, main body member may be formed from an inner polymeric tubular member, an outer polymeric jacket, and a stranded reinforcement member, such as a stainless steel braid, disposed between the inner tubular member and the outer jacket. Suitable polymeric materials include polyurethane, polyamides, fluoropolymers such as polytetrafluoroethylene, and the like. In some embodiments, the main catheter is steerable, e.g. as discussed in more detail below, and may be formed in accordance with the teaching presented in U.S. Pat. No. 6,836,687 to Kelley, entitled, Method and System for delivery of a medical electrical lead within a venous system, issued on Dec. 28, 2004; U.S. Pat. No. 6,059,739 to Baumann, entitled Method and apparatus for deflecting a catheter or lead, issued May 9, 2000; U.S. Pat. No. 7,037,290 to Gardeski, entitled Multi-lumen steerable catheter, issued May 2, 2006; or the like.

The body 310 of the side sheath 300 may be formed of any collapsible and expandable material. For example, the body 310 of the side sheath 300 may be formed from a thin sheet of nylon or polyester that is folded to assume a collapsed configuration. Techniques for folding balloons of balloon angioplasty catheters may be employed to form a collapsed side sheath. The folding may be performed manually or by a machine, as known in the art.

In the embodiments depicted in FIGS. 3 and 4A, the protrusion of the side sheath 300 from the main body member 210 in the collapsed configuration is exaggerated for the purposes of illustration. Generally, the cumulative profile of the side sheath 300 and the main body member 210 is substantially similar to the profile of the main body member 210 alone. That is, the overall outer diametric dimension of the side sheath 300 and the main body member 210, when the side sheath 300 is in a collapsed configuration, is preferably less than 1.25 times the outer diametric dimension of the main body 210. For example, the cumulative diametric dimension of the collapsed side sheath and the main body may be between 1 and 1.15 times the outer diametric dimension of the main body.

The cumulative low profile of the introducer 200, when the side sheath 300 is in a collapsed configuration, facilitates percutaneous introduction of the lead into the patient. When the introducer 200 is properly positioned in the patient, the side sheath 300 may be expanded and a lead inserted. In various embodiments, insertion of the lead into the side sheath 300 causes or facilitates expansion of the side sheath. In some embodiments, it may be desirable to introduce fluid, such as saline, to facilitate or cause expansion of the side sheath 300. The fluid may serve a lubricating purpose, particularly if the body member 310 of the side sheath 300 is formed from hydrophilic material, facilitating insertion of the lead.

Figure 5A:
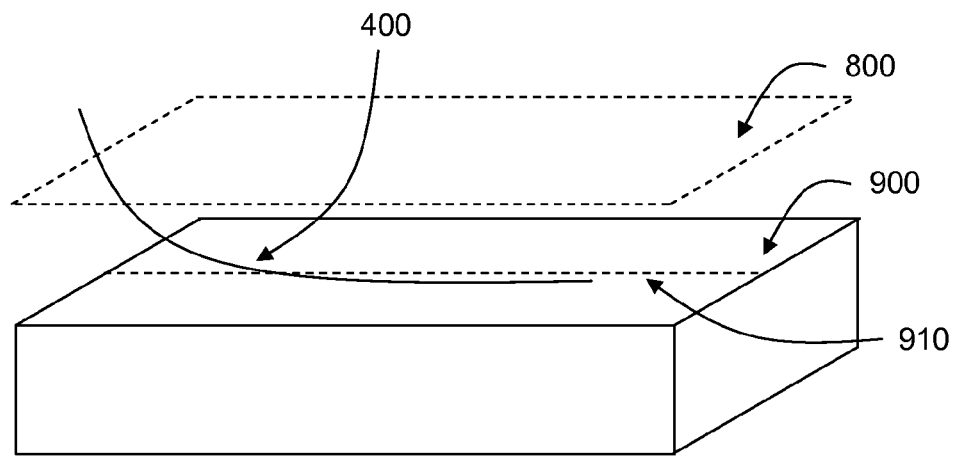
FIGS. 5A-F are schematic views showing steps of an embodiment of a method for implanting two leads having distal end portions, where the distal end portions are implanted parallel to each other and on either side of the midline of a spinal cord.
Figure 5B:
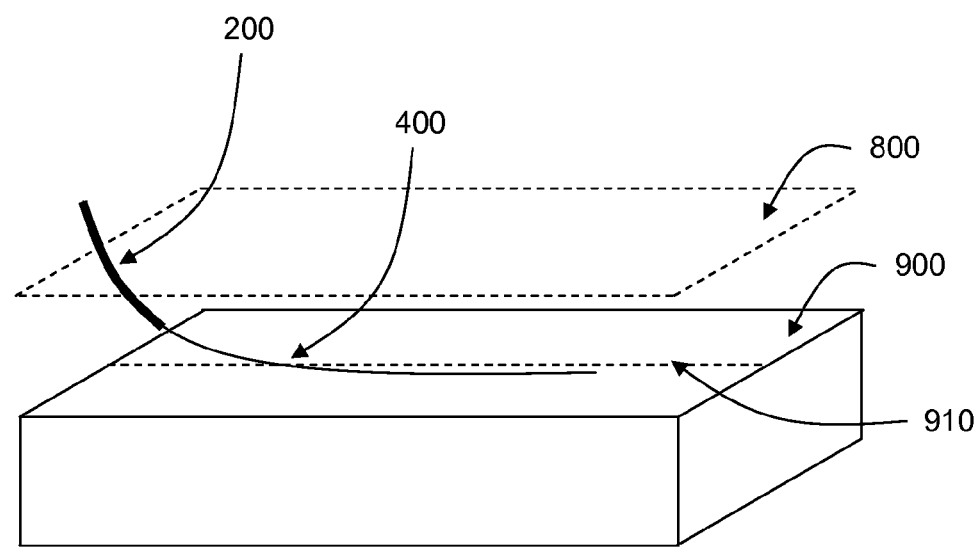
Figure 5C:
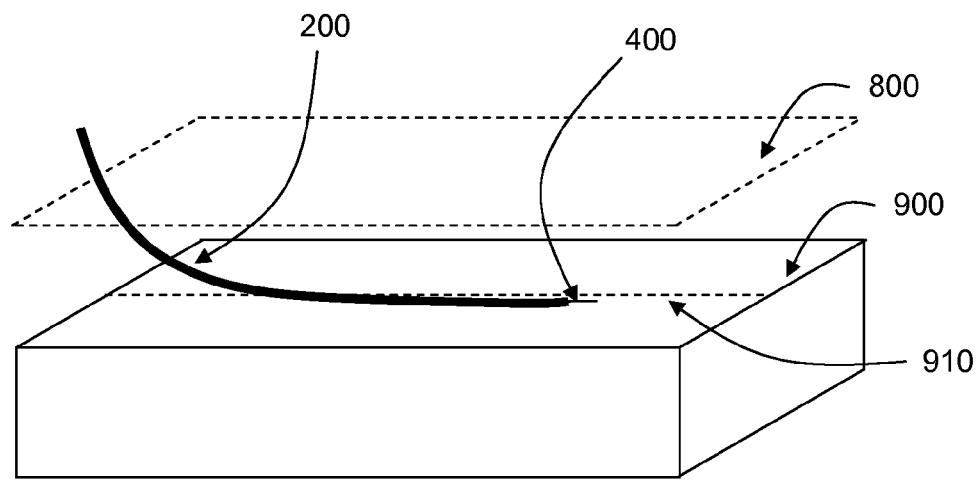
Figure 5D:
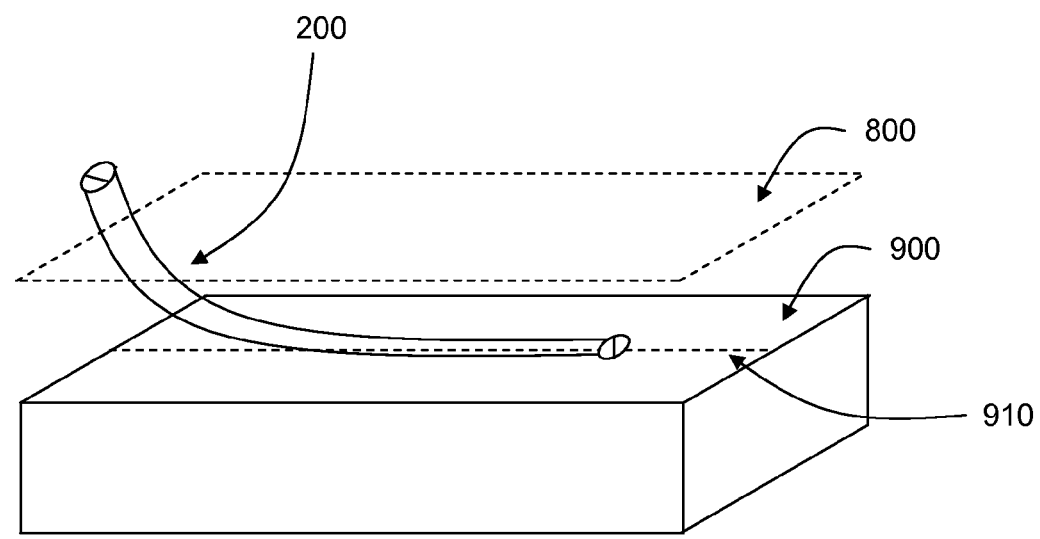
Figure 5E:
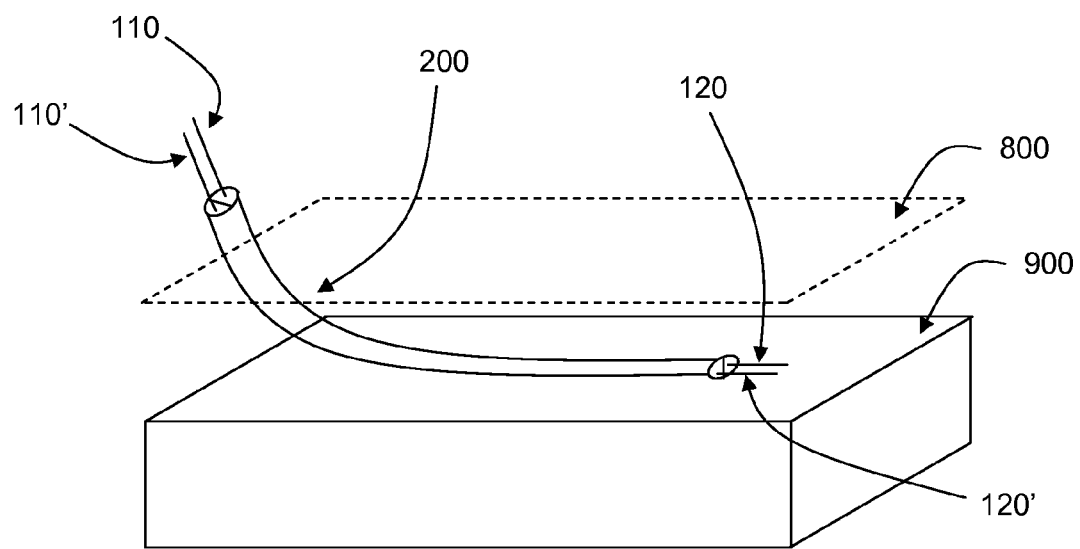
Figure 5F:
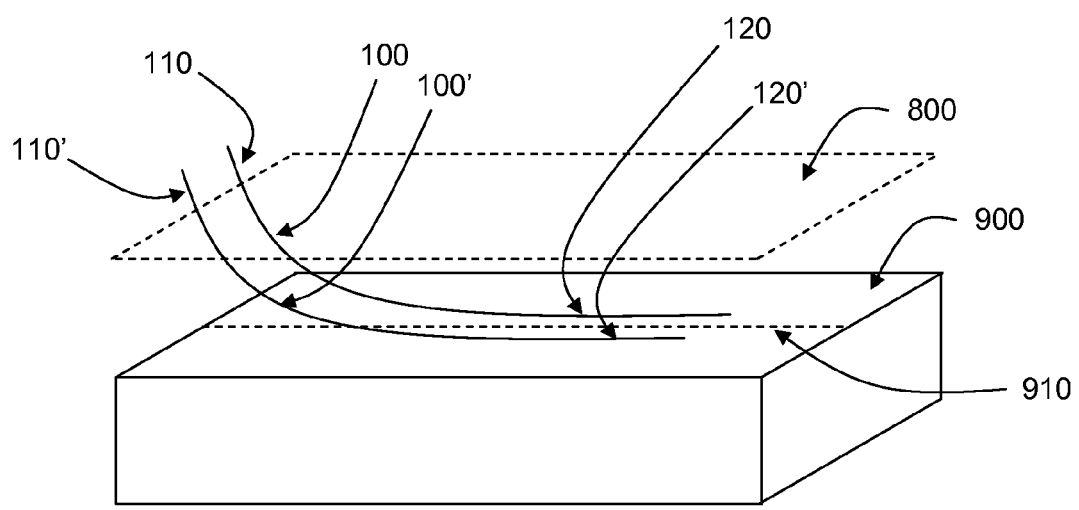

Referring now to FIGS. 5A-F, schematic drawings illustrating a method for percutaneously implanting leads 100, 100' on either side of the midline 910 of a spinal cord 900 of a patient are shown. An introducer 200 similar to that shown in FIG. 3 may be used in accordance with the method depicted in FIGS. 5A-5F. As shown in FIG. 5A, a guide wire 400 is percutaneously inserted through the patient's skin 800 and positioned epidurally along one side of midline 910 of the spinal cord 900. An introducer 200 is inserted over the proximal end of the guide wire 400 and advanced through the skin 800 into the epidural space of the spinal cord 900 (see FIGS. 5B-C). The lumen of the main body of an introducer (see e.g., FIG. 3) may be advanced over the guidewire. Once the introducer 200 is properly positioned along the spinal cord 900, the guidewire 400 may be withdrawn from the introducer 200, leaving the introducer 200 in place (see FIG. 5D). The side sheath is expanded resulting in two lumens for introduction of leads, with each lumen on opposing sides of the midline (see FIG. 5D). Referring now to FIGS. 5E-F, a first lead 100 may be advanced through the main lumen of the introducer 200, and a second lead 100' may be inserted through the expanded side lumen of the side sheath. The introducer 200 may be withdrawn, leaving the leads 100, 100' in place. In the depicted embodiment, the distal end portions 120, 120' of the leads 100, 100' are positioned along either side of the midline 910 of the spinal cord 900, which is a desirable orientation for spinal cord stimulation of the dorsal horn. The proximal end portions 110, 110' of the leads 100, 100' extend external to the skin 800, and are, in some embodiments, connected to an implantable medical device (not shown), such as an electrical signal generator, in a subcutaneous location, leaving the entire length of the leads 100, 100' implanted in the patient.

Figure 6:
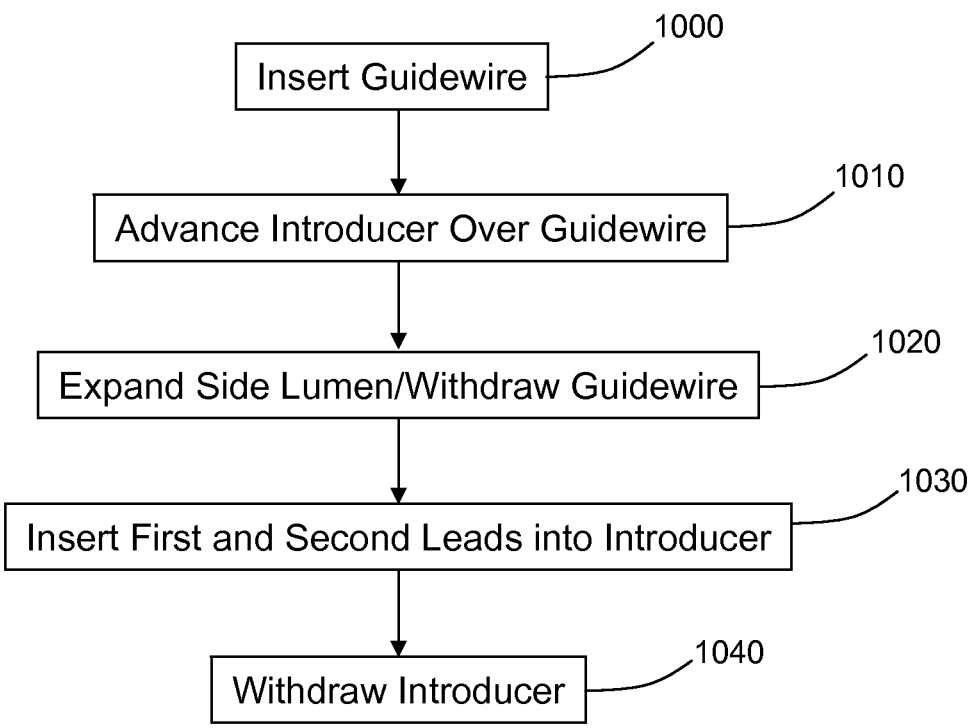
FIG. 6 is a flow diagram of a method for implanting two leads using a device similar to the device depicted in FIG. 3.

Referring now to FIG. 6, a flow diagram describing an overview of some steps of a method for introducing two leads into a patient. The depicted method is similar to the steps depicted in FIGS. 5A-F and may be used with an introducer as depicted in FIG. 3. The method includes inserting a guidewire into a patient (1000). The guidewire may be inserted along one side of and parallel to the midline of the spinal cord in the epidural space (e.g., as depicted in FIG. 5A). An introducer may then be introduced over the guidewire (1010). For example, the main lumen 210 of the introducer 200 depicted in FIG. 3 may be advanced over the guidewire, with the side sheath 300 collapsed to keep a low profile to facilitate advancement and insertion. The guide wire may be withdrawn and the side sheath expanded (1020). The side sheath may be expanded prior to, during or after withdrawal of the guidewire. In some embodiments, such as the embodiment depicted in FIGS. 5A-F, the introducer is positioned such that expansion of the side sheath results in the lumen of the side sheath being positioned on the opposite side of the midline of the spinal cord as the lumen of the main body of the introducer. A first lead may be inserted into the main lumen of the introducer, and a second lead may be inserted into the lumen of the side sheath (1030).

It will be understood that insertion of the second lead into the lumen of the side sheath may be a part of, or the cause of, the expansion of the side sheath. The leads may be introduced in any order. In some embodiments, it may be desirable to introduce the second lead in the side sheath while the guidewire remains in the lumen of the main body. Thus, a test stimulation pulse may be administered by the second lead to verify proper positioning of the lead and introducer. If, via the test stimulation, the lead or introducer is determined to be improperly located, the guide wire, and thus the introducer, can be readily moved to another location. Still with reference to FIG. 6, once the leads are properly positioned, the introducer may be withdrawn, leaving the leads positioned in the proper location and orientation (e.g., along either side of the midline of the spinal cord such that the distal end portions are parallel to each other and the midline).

Referring now to FIGS. 7A-B, an alternative embodiment of a lead introducer 200 is shown (alternative relative to FIGS.

3-4). In the depicted embodiment, the introducer 200 has a main body member 210 defining a lumen 220 extending therethrough. The depicted introducer 200 includes first 300 and second 300' side sheaths attached to the main body 210. The side sheaths 300, 300' have a main body member 310, 310' defining a lumen 320, 320' running therethrough. The side sheaths 300, 300' are in a collapsed configuration in FIG. 7A and are in an expanded configuration in FIG. 7B. In the expanded configuration, the lumens 320, 320' of the side sheaths 300, 300' are configured to slidably receive a lead. Preferably, the side sheaths 300, 300' are in an unstressed state in the expanded configuration. A first lead may be inserted in the first side sheath 300 and a second lead may be inserted in the second side sheath 300' while a guidewire is maintained within the lumen 220 of the main body 210. Such a configuration can allow for ready movement of the introducer if test stimulation of the leads indicates improper placement.

The lumens 320, 320' of the side sheaths 300, 300', in their expanded configurations, and the lumen 220 of the main body 210 are depicted as having collinear axes in FIG. 7B. However, it will be understood that the lumens need not be co-linear. Regardless of whether the axes of the lumens are co-linear, the side sheaths 300, 300' are attached to the main body 210 on generally opposing sides of the main body 210.

As with the introducer depicted in FIGS. 3-4, the protrusion of the side sheaths 300, 300' in FIG. 7A in the collapsed configuration are exaggerated for the purpose of illustration. Generally, the cumulative profile of the side sheath 300 or 300' and the main body member 210 is substantially similar to the profile of the main body member 210 alone. That is, the overall outer diametric dimension of the main body member 210 and side sheath 300 or 300', when the side sheath 300 or 300' is in a collapsed configuration, is preferably less than 1.25 times the outer diametric dimension of the main body 210. For example, the cumulative diametric dimension of the collapsed side sheath and the main body may be between 1 and 1.15 times the outer diametric dimension of the main body.

The cumulative low profile of the introducer 200, when the side sheaths 300, 300' are in a collapsed configuration, facilitates percutaneous introduction of the lead into the patient. When the introducer 200 is properly positioned in the patient, the side sheath 300 may be expanded and leads inserted. In various embodiments, insertion of the lead into the side sheaths 300, 300' causes or facilitates expansion of the side sheath. In some embodiments, it may be desirable to introduce fluid, such as saline, to facilitate or cause expansion of the side sheaths 300, 300'. The fluid may serve a lubricating purpose, particularly if the body members 310, 310' of the side sheaths 300, 300' are formed from hydrophilic material, facilitating insertion of the leads.

An introducer 200 as depicted in FIG. 7 may be made from any suitable material via any suitable process (e.g., as described above with regard to the introducer depicted in FIGS. 3-4).

An overview of a method for implanting two leads using an introducer similar to that depicted in FIGS. 7A-B is shown in the flow diagram of FIG. 8. The method includes inserting a guidewire in a patient (2000), advancing the introducer over the guidewire (2010) with the side sheaths in a collapsed configuration, expanding the side sheaths (2020), inserting a first lead in the first side sheath and inserting a second lead into the second side sheath (2030), and withdrawing the introducer and guidewire (2040), leaving the leads implanted in the proper position and orientation in the patient. It will be understood that inserting the leads in the side sheathe (2030) may be a part of, or the cause of, expanding the side sheaths (2030).

Figure 9A:
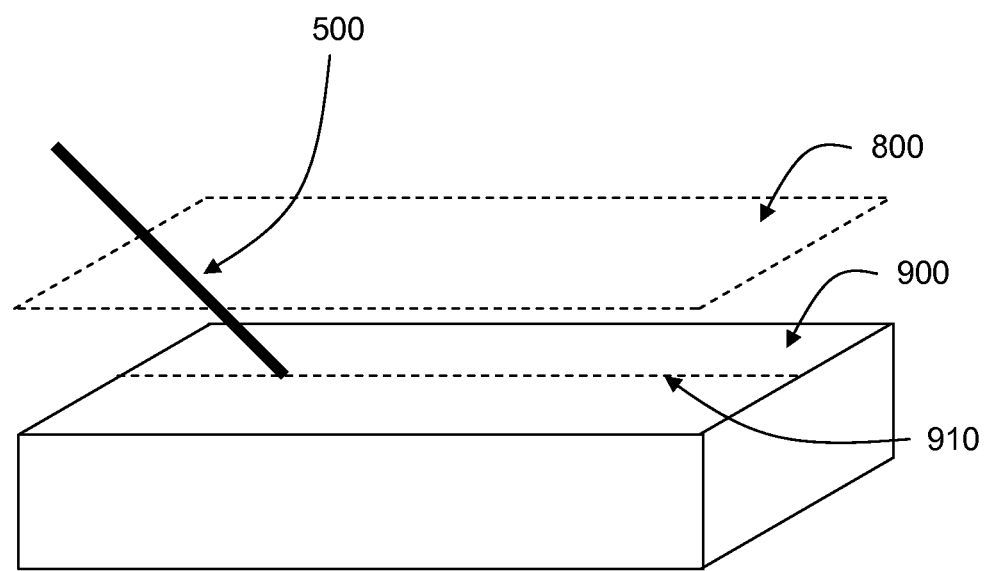
FIGS. 9A-F are schematic views showing steps of an embodiment of a method for implanting two leads having distal end portions, where the distal end portions are implanted parallel to each other and on either side of the midline of a spinal cord.
Figure 9B:
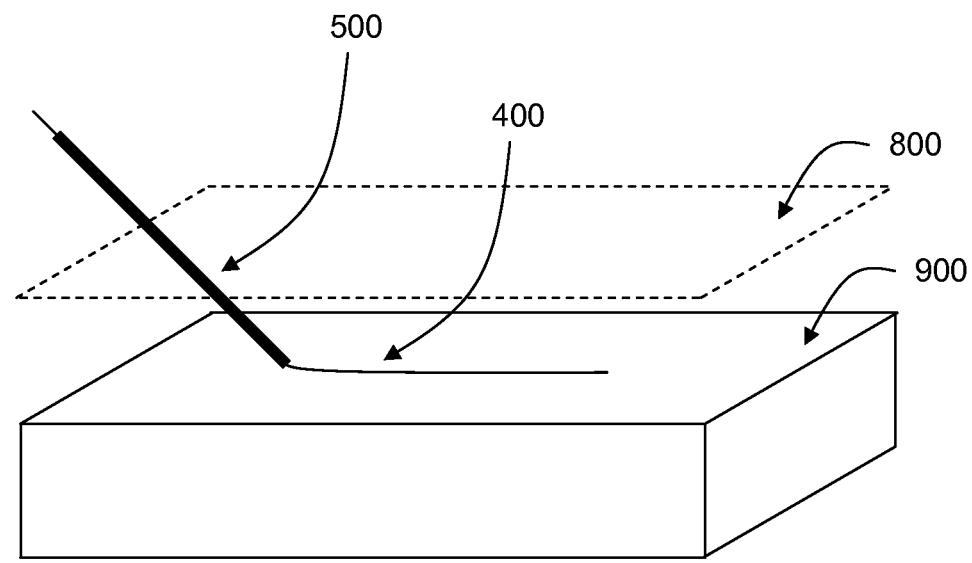
Figure 9C:
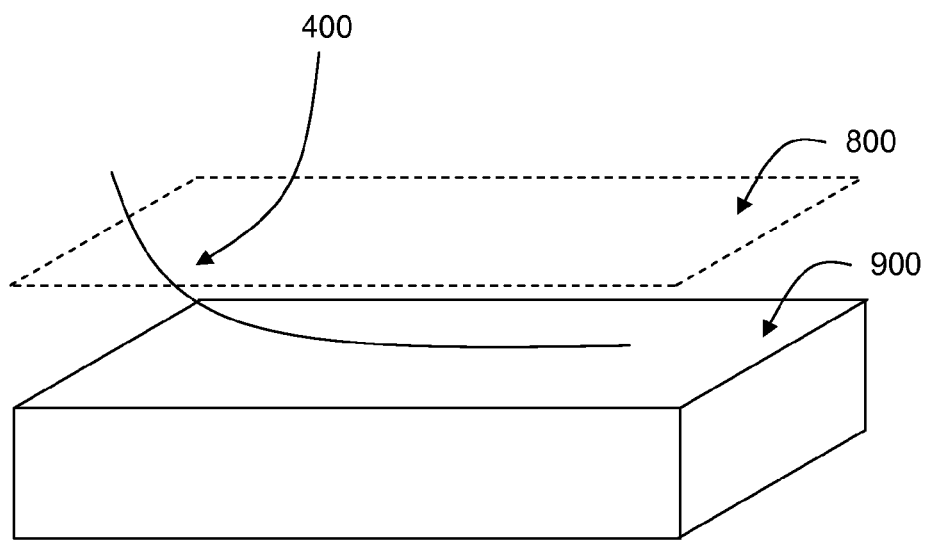
Figure 9D:
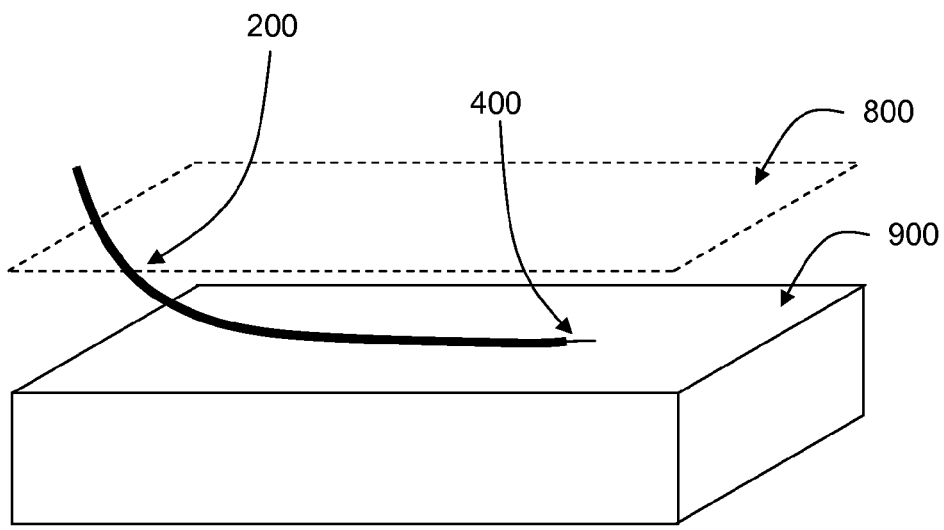
Figure 9E:
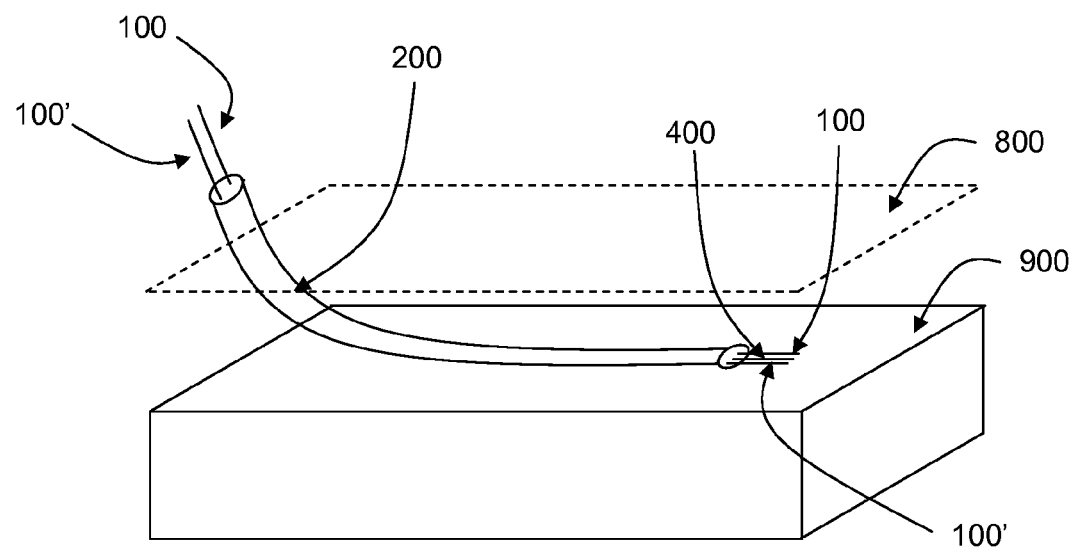
Figure 9F:
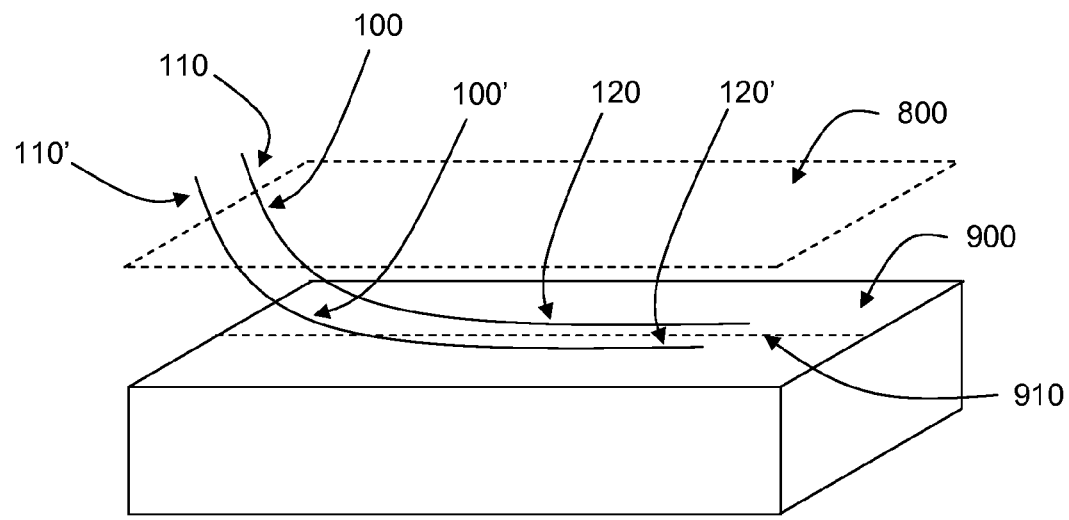

Referring now to FIGS. 9A-9F, schematic views of a method employing an introducer 200 as depicted in FIGS. 7A-B are shown. In FIG. 9A, a needle 500 is percutaneously inserted through the skin 800 to gain accesses to the epidural space in proximity to the midline 910 of the spinal cord 900. A trochar (not shown) may be inserted into the lumen of the needle to prevent tissue from entering the lumen as the needle passes through the skin. A guide wire 400 is then advanced through the needle 500, into the epidural space along the midline of the spinal cord 900 (see FIG. 9B). The needle 500 is then removed, leaving the guidewire 400 in place (see FIG. 9C). As shown in FIG. 9D, the introducer 200 may then be advanced over the guidewire 200, such that the introducer 200 is positioned along the midline of the spinal cord. By way of example, the introducer 200 depicted in FIGS. 7A-B may be advanced over the guidewire 400 such that the guidewire 400 is received in the lumen 220 of the main body 210 (see, e.g., FIGS. 7A-B). The side sheaths may be expanded and first 100 and second 100' leads may be inserted into the first and second side sheaths, respectively, while the guidewire 400 remains in the introducer 200 (see FIG. 9E), such that the leads 100, 100' are positioned on either side of the midline of the spinal cord 900. The introducer 200 and guidewire 400 may be withdrawn, leaving the leads 100, 100' implanted (see, FIG. 9F). In the depicted embodiment, the distal end portions 120, 120' of the leads 100, 100' are positioned along either side of the midline 910 of the spinal cord 900, parallel to each other and the midline, which is a desirable orientation for spinal cord stimulation of the dorsal horn. The proximal end portions 110, 110' of the leads 100, 100' extend external to the skin 800. As discussed above with regard to FIG. 5F, the leads may be connected to an implantable medical device (not shown), such as an electrical signal generator, in a subcutaneous location, leaving the entire length of the leads 100, 100' implanted in the patient.

Figure 10:
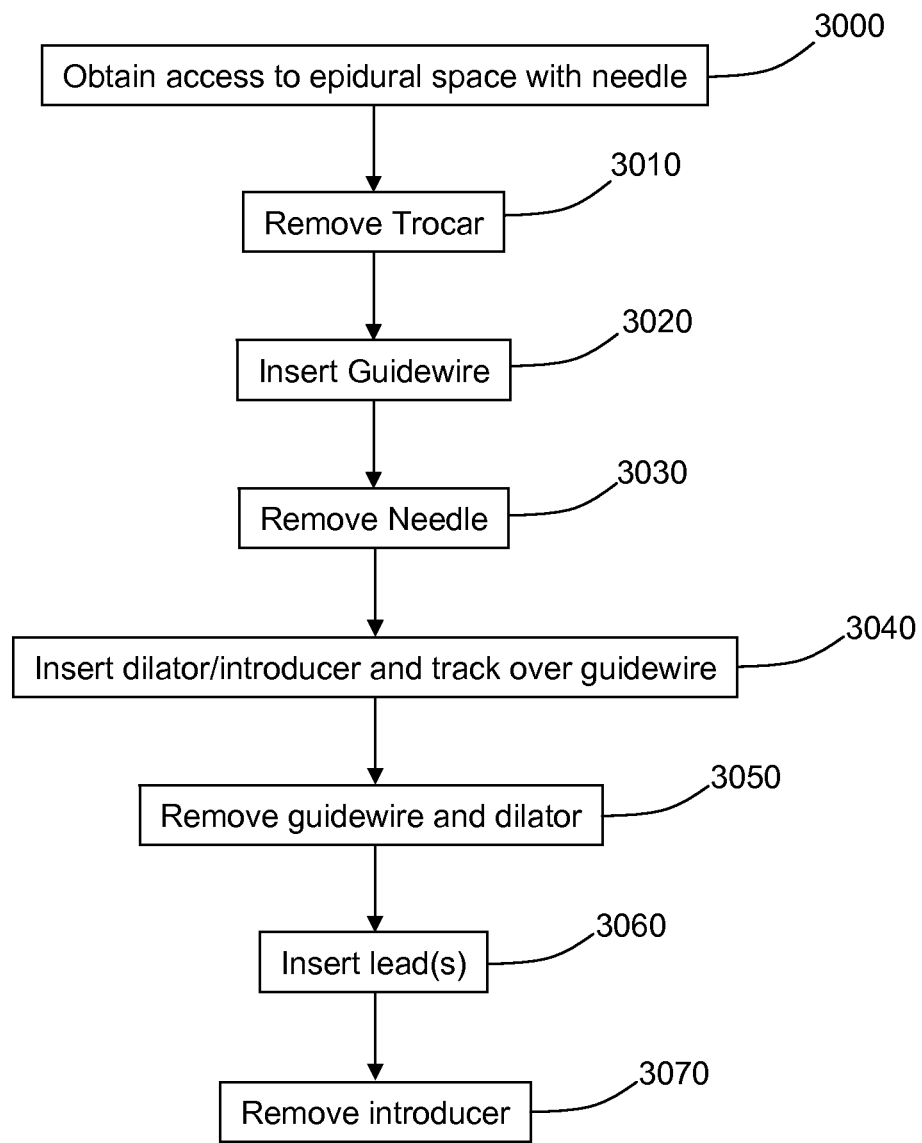
FIG. 10 is a flow diagram illustrating an embodiment of a method for implanting one or more leads.

Referring now to FIG. 10, a method that may be employed for inserting leads along a spinal cord using an introducer as described herein is depicted in a flow diagram. In many respects the method depicted in FIG. 10 is similar to the schematic method depicted in FIGS. 9A-F. The method depicted in FIG. 10 includes obtaining access to the epidural space with a needle (3000). If a trochar is used to prevent tissue from entering the lumen of the needle, the trochar is removed once the needle is properly positioned in the epidural space (3010). A guidewire is then inserted into the needle (3020) and advanced to an appropriate position along the spinal cord. For example, if an introducer as depicted in FIG. 3 is employed, the guidewire may be positioned parallel to the midline along one side of the midline. If an introducer as depicted in FIG. 7 is employed, the guidewire may be positioned parallel to the midline and along the midline. A dilator (which will be discussed in more detail below with regard to FIG. 11) may be introduced into the main lumen of an introducer and the dilator/introducer may be tracked over the guidewire (3050). The guidewire and dilator may then be removed (e.g., if an introducer as depicted in FIG. 3 is employed) (3050), leaving the introducer in place. The side sheath(s) may be expanded and leads inserted (3060). Once the leads are properly inserted, the introducer may be withdrawn (3070).

Figure 11:
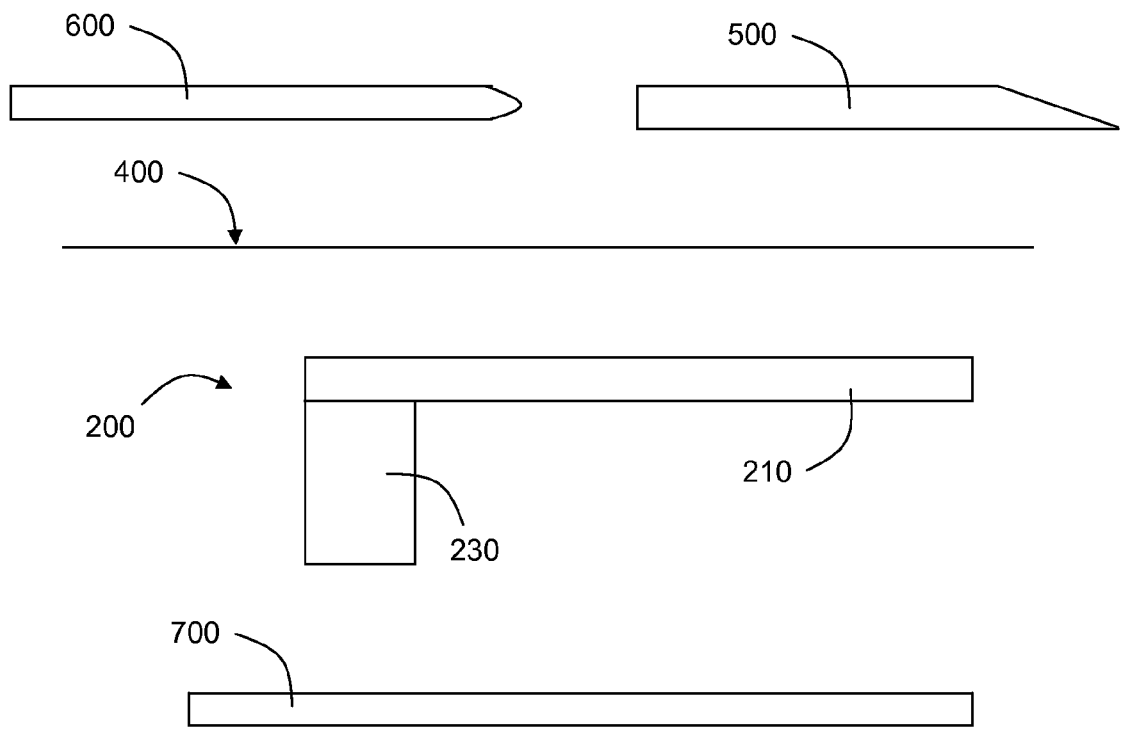
FIG. 11 is a schematic side view of devices of an embodiment of a system for implanting leads.
Figure 12:
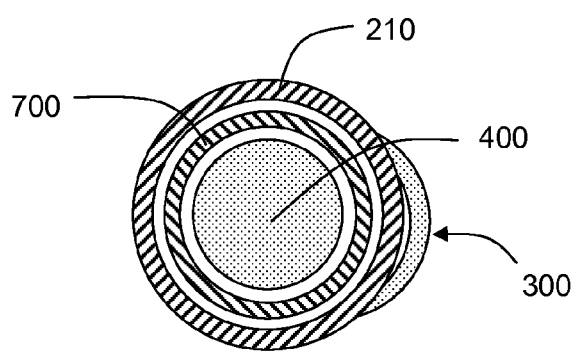
FIG. 12 is a schematic cross-section of a guidewire disposed in a lumen of a dilator, which is disposed within a lumen of an introducer.

Referring now to FIGS. 11-12, components of a system that may be employed to carry out the method described in FIG. 10 are shown. As shown in FIG. 11, the system may include a trochar 600, a needle 500, a guidewire 400, an introducer 200, and a dilator 700. The depicted introducer 200 includes a handle 230 that may include an actuation mechanism for use in steering the main body 210 (e.g, as described in more detail below with regard to FIGS. 16-18). The dilator 700 includes a lumen configured to receive the guidewire 400 and is configured to be slidably received by the lumen of the main body member 210 of the introducer 200 (see FIG. 12). The dilator 400 is preferably formed of a higher durometer material than the main body 210 of the introducer 200 (at least the material surrounding the lumen of the main body 210) to aid in movement of the introducer along the guidewire 400. The dilator 700 may be made of any suitable material, such as nylon, nylon-blend, polyetheretherketone (PEEK), polytetrafluoroethylene (PTFE), high density polyethylene (HDPE), or the like.

As shown in FIG. 12, the introducer may have one or more side sheaths 300 attached to the main body 210.

Figure 13:
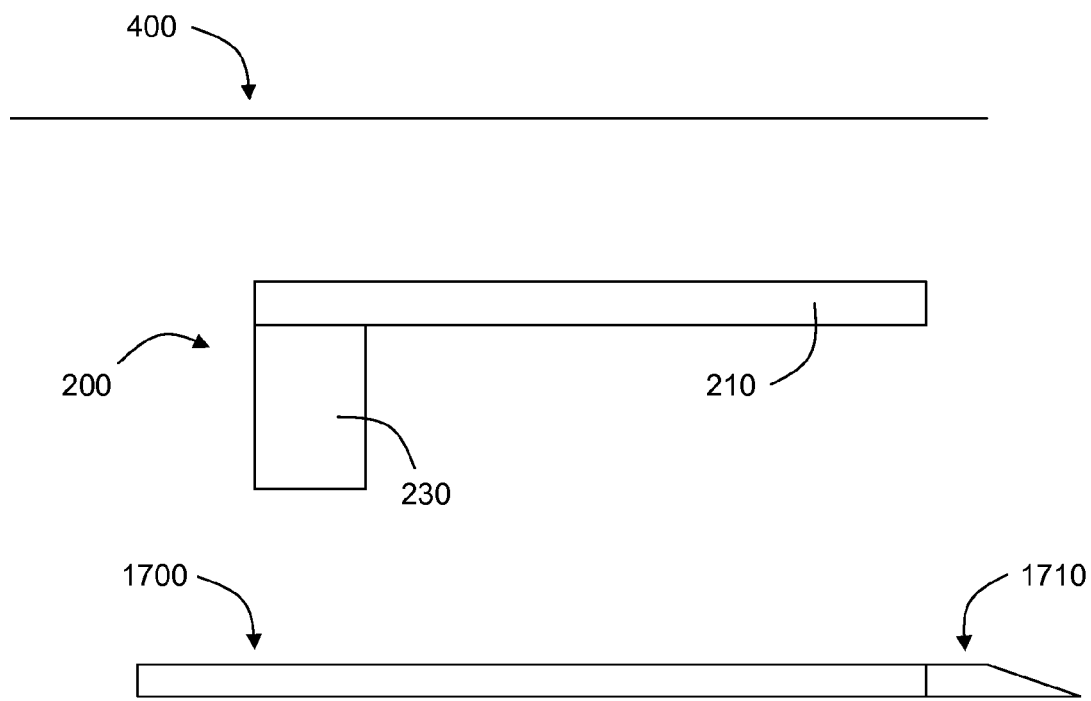
FIG. 13 is a schematic side view of devices of an embodiment of a system for implanting leads.
Figure 14:
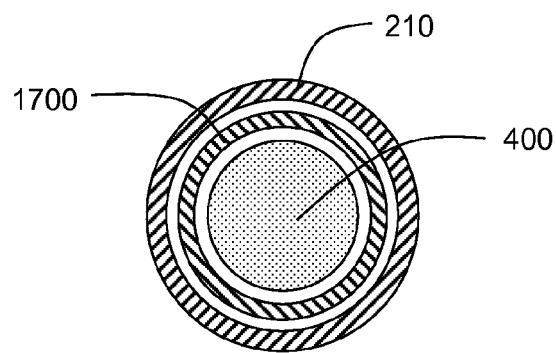
FIG. 14 is a schematic cross-section of a guidewire disposed in a lumen of a dilator, which is disposed within a lumen of an introducer.

Referring now to FIGS. 13-14, components of an alternative embodiment of a system that may be employed to implant one or more leads. The system includes a guidewire 400, an introducer 200, and a dilator 1700. Like the system depicted in FIG. 11, the introducer includes a handle 230 that may have an actuation mechanism for use in steering the main body member 210. Unlike the system depicted in FIG. 11, the dilator 1700 depicted in FIG. 13 includes a needle tip 1710 that may take the place of the needle depicted in FIG. 11. By using a needle-tipped dilator 1700, the process for implanting leads may be expedited. For example, rather than inserting a needle, tracking a guidewire through the needle, and withdrawing the needle prior to tracking the dilator /introducer over the guidewire, the dilator/introducer may be put in place, guidewire inserted, and the introducer positioned.

As with the system depicted in FIGS. 11-12, the dilator 1700 depicted in FIG. 13 includes a lumen configured to receive the guidewire 400 and is configured to be slidably received by the lumen of the main body member 210 of the introducer 200 (see FIG. 14). While not shown in FIG. 14, the introducer may have one or more side sheaths attached to the main body (e.g., as described above with regard to FIGS. 3, 4, and 7). However, in some embodiments, the introducer of the system depicted in FIG. 13 does not have any side sheaths.

The needle tip 1710 of the dilator 1700 may be formed from any suitable material, such as stainless steel. The needle tip 1710 may be formed from the same material as the remainder of the dilator or may be attached (e.g., bonded, welded, adhered, or the like) to the main body of the dilator 1700.

Figure 15:
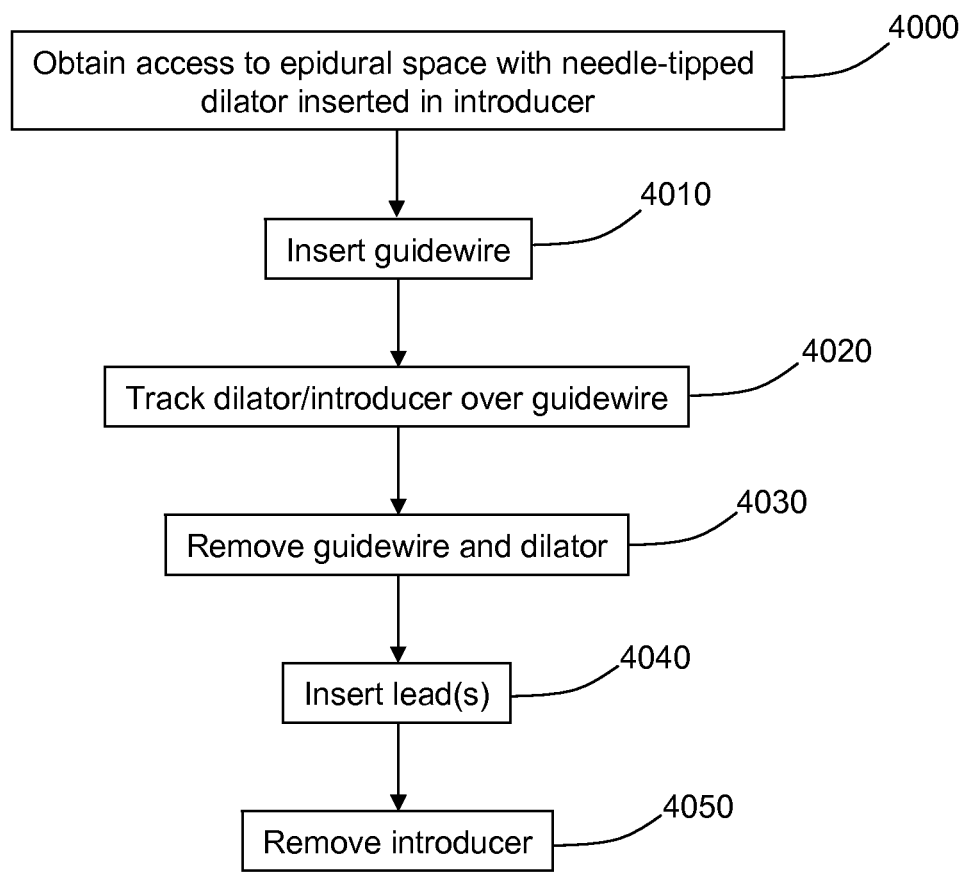
FIG. 15 is a flow diagram illustrating an embodiment of a method for implanting one or more leads.

A method for inserting one or more leads employing a system as depicted in FIGS. 13-14 is shown in the flow diagram of FIG. 15. The method includes obtaining access to the epidural space with the needle-tipped dilator, which is pre-inserted into the lumen of the main body of the introducer (4000). A guidewire is then inserted through the lumen of the dilator and advanced to a desired location of the patient (4010). The dilator and introducer are tracked over the guidewire to the desired location (4020), and the dilator and guidewire are removed (4030), leaving the introducer in place. A lead may be inserted into the main lumen of the introducer or any side sheaths, if present (4040). The introducer may be withdrawn over the lead(s) (4050), leaving the lead(s) in place.

Figure 16:
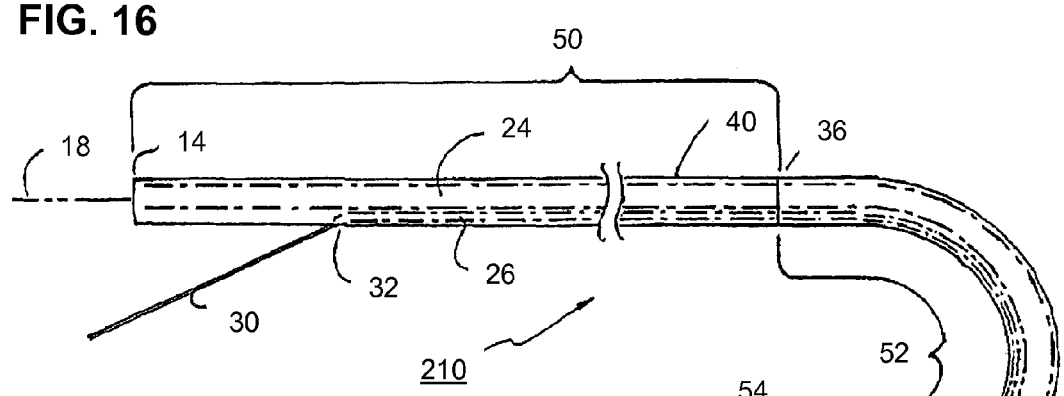
FIG. 16 is a schematic plan view of an embodiment of a main sheath body of a steerable introducer.
Figure 17:
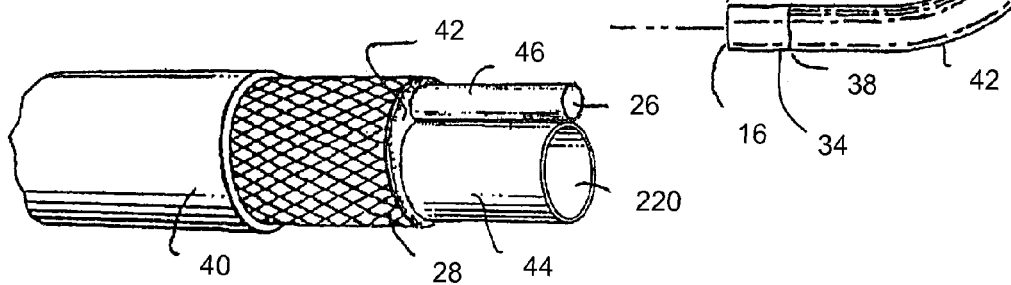
FIG. 17 is a schematic perspective view of a section of an embodiment of the main sheath body depicted in FIG. 16.
Figure 18:
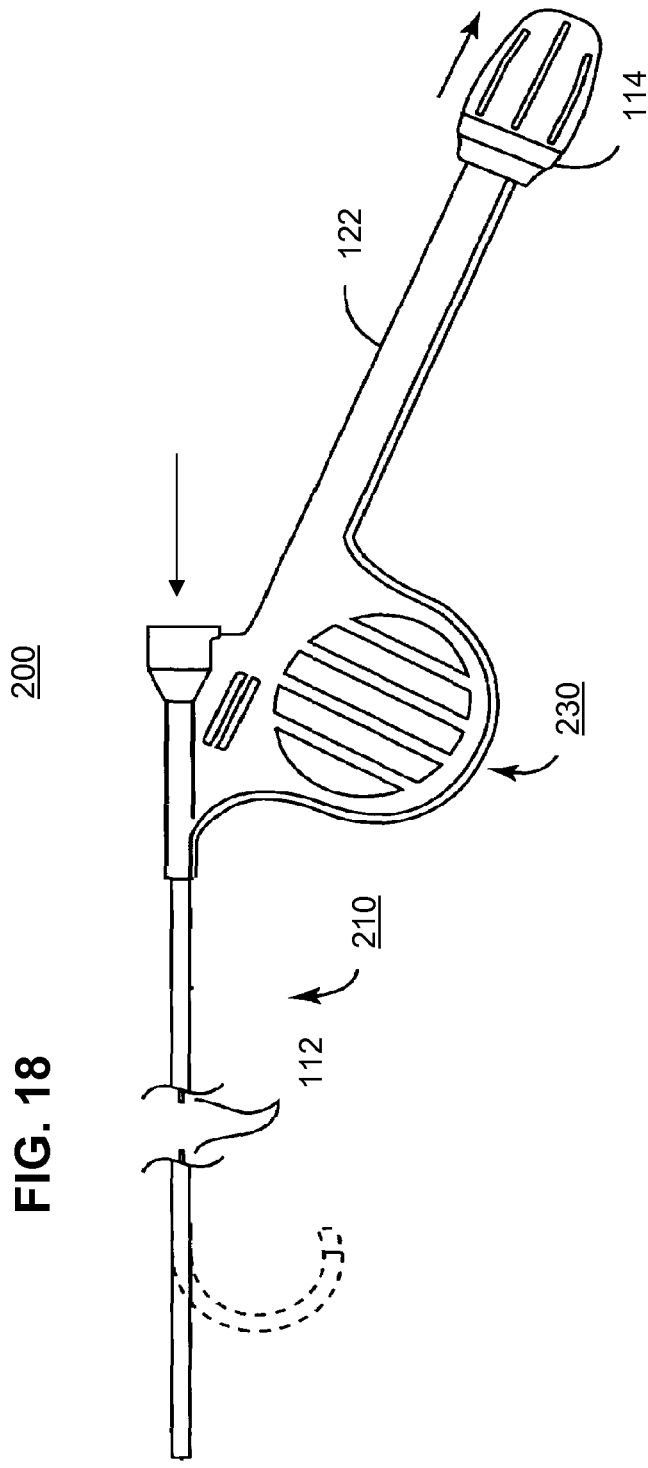
FIG. 18 is a schematic plan view of an embodiment of a steerable introducer employing a pull wire as indicated in FIGS. 16-17.

Referring now to FIGS. 16-18, a steerable introducer 200 is shown. The main body 210 sheath is deflectable so that the introducer may be steered as desired to facilitate placement of a lead. When the introducer is steerable, the introducer may be steered in the epidural space after the guide wire has been withdrawn.

A steerable introducer may be formed as know in the art. For example, a steerable introducer may incorporate one or more aspects of U.S. Pat. No. 7,037,290 to Gardeski, entitled Multi-lumen steerable catheter, issued May 2, 2006; U.S. Pat. No. 6,059,739 to Baumann, entitled Method and apparatus for deflecting a lead or catheter, issued May 9, 2000; U.S. Pat. No. 6,836,687 to Kelley, entitled Method and system for delivery of a medical electrical lead within a venous system, issued Dec. 28, 2004; or the like. In some embodiments, a Medtronic, Inc. Model 6227 deflectable catheter for left heart placement may be used or modified to serve as an introducer for use in accordance with the teachings presented herein. For the purposes of illustration, an embodiment of a steerable introducer that may be used in accordance with the teachings herein is depicted in FIGS. 16-18. While not shown, it will be understood that the main body 210 of the introducer 200 may have one or more attached collapsible and expandable side sheaths (e.g., as depicted in FIGS. 3, 4, and 7).

FIG. 16-17 depict a multi-lumen catheter body 210 that may incorporate a bend induced in the intermediate segment 52 thereof. The elongated main body 210 has a main body axis 18 and extends from a main body proximal end 14 adapted to be coupled with a hub to a main body distal end 16. A delivery lumen 220 extends through the main body 210 from a delivery lumen proximal end opening at the main body proximal end 14 to a delivery lumen distal end opening at the main body distal end 16. An "accessory" or deflection lumen 26 extends alongside the delivery lumen 220 through the main body 210 from a deflection lumen proximal end opening 32 through sheath 34 to either a deflection lumen closed distal end proximal to the main body distal end 16 or a deflection lumen distal end opening at the main body distal end 16, depending upon the type of steerable catheter formed with the steerable main body 210.

The main body 210 may include a number of segments, e.g., segments 50, 52 and 54, along its length formed of different materials and structural components to provide different handling characteristics. The segments 50 and 52 are formed of respective outer sheath segments 40 and 42 of materials that contribute to making the most proximal segment 50 relatively stiff to impart column strength and torqueability and to making intermediate segment 52 more flexible and bendable upon manipulation of the deflection mechanism. The distal segment 54 incorporates a soft sheath 34 that is intended to be atraumatic at main body distal end 16 to avoid injury to tissue. Intermediate segment 52 is axially joined to proximal segment 50 at junction 36, and the intermediate segment 52 is joined to distal segment 54 at junction 38.

The deflection lumen 26 is adapted to receive a deflection mechanism 30 extended through in the outer sheath side opening 32 operable to selectively impart a bend in the intermediate segment 52 of the main body 210. The deflection mechanism 30 shown schematically in FIG. 16 includes one of a permanently inserted and distally attached pull wire, a removable stylet, a removable guide wire or conductors for applying current to and resistively heating a shape memory alloy strip inserted into the intermediate segment 52. The removable stylet can be a steerable stylet of the types described in commonly assigned U.S. Pat. Nos. 5,873,842 and 6,146,338, for example.

Referring to FIG. 17, the main body 210 is formed of a proximal outer sheath segment 40 and an intermediate outer sheath segment 42 encasing a tubular wire braid 28, a delivery lumen liner 44 defining delivery lumen 220, and a deflection lumen liner 46 defining the deflection lumen 26. The delivery and deflection lumen liners 44 and 46 may have a substantially uniform cross-sectional area along the lengths thereof or may vary along the lengths thereof. It is desirable for the main body 210 to be constructed to assure that the delivery and deflection lumens 220 and 26 maintain their cross-sectional shape and to provide the desired flexibility, pushability, torqueability and low profile of the main body 210 desired for its intended use in a steerable catheter. It is further desirable that the inner surfaces of the lumen liners 44 and 46 are lubricious to enable free passage or movement of devices therethrough. It is also desirable that the lumen liners 44 and 46 resist rupture or penetration.

An example of a steerable introducer 200 employing a main body 210 sheath as depicted in FIGS. 16-17 is shown in FIG. 18. In the embodiment depicted in FIG. 18, a hub or handle 230 is attached to the main body proximal end 14. The hub body 230 includes an elongated side port extension 122. The deflection mechanism 30 (see FIG. 16) of the steerable introducer 200 includes a pull wire 112 operably coupled to proximal knob 114, which can be pulled to deflect the distal end portion of the main body 210 and released to straighten the distal end portion. Of course any other suitable actuation member, such as a rotating member with associated sliding member that causes pulling or relaxing of the wire 112 to deflect the main body 210 of the introducer may be employed. In the embodiment depicted in FIG. 18, a lead, dilator, or guidewire may be introduced through the main lumen of the main body member 210 as indicated by the depicted arrow.

While much of the description and drawings presented are directed to placement of leads parallel to each other and parallel to the midline of the spinal cord, it will be understood that the devices, systems and methods described herein may be employed to implant leads in any suitable configuration, such as parallel to each other but not parallel to the midline, parallel to each other but on the same side of the midline, parallel to each other bit off-center from the midline, at an anatomical location removed from the midline, or the like.

Thus, embodiments of the INTRODUCER FOR LEAD DELIVERY are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method for implanting first and second leads along a spinal cord of a patient, comprising
    inserting a guidewire in proximity to the patient's spinal cord;
    inserting an introducer in proximity to the patient's spinal cord by advancing the introducer over the guidewire, wherein the introducer has a first lumen configured to receive the guidewire and a second lumen, the second lumen having a collapsed configuration and an expanded configuration, wherein the second lumen is in the collapsed configuration as the introducer is inserted;
    expanding the second lumen to the expanded configuration;
    inserting the first lead into the first lumen of the introducer;
    inserting the second lead into the expanded second lumen; and
    withdrawing the introducer and leaving the first and second leads implanted along the spinal cord.

2. The method of claim 1, wherein expanding the second lumen comprises inserting the second lead into the second lumen.

3. The method of claim 1, wherein expanding the second lumen comprises infusing a fluid into the second lumen.

4. The method of claim 1, further comprising inserting a dilator into the first lumen of the introducer, and wherein advancing the introducer over the guidewire comprises advancing the dilator over the guidewire.

5. The method of claim 4, wherein the dilator comprises a needle tip configured to puncture the patient's skin, and wherein the method further comprises percutaneously inserting the needle tip of the dilator into the patient.

6. A method for implanting first and second leads along a spinal cord of a patient comprising:
    providing an introducer having a first lumen and a second lumen, the second lumen having a collapsed configuration and an expanded configuration, wherein the second lumen is in the collapsed configuration as the introducer is inserted;
    inserting a needle-tipped dilator through the first lumen of the introducer to preload the dilator in the introducer, wherein the dilator has a lumen;
    inserting a guidewire through the lumen of the dilator such that the guidewire is in proximity to the patient's spinal cord;
    percutaneously inserting the introducer and preloaded dilator into the patient's epidural space in proximity to the patient's spinal cord by advancing the preloaded dilator over the guidewire; and
    withdrawing the dilator and the guidewire, leaving the introducer in proximity to the patient's spinal cord;
    expanding the second lumen to the expanded configuration;
    inserting the first lead into the first lumen of the introducer;
    inserting the second lead into the expanded second lumen; and
    withdrawing the introducer and leaving the first and second leads implanted along the spinal cord.

7. The method of claim 6, wherein the main body of the introducer is steerable.

8. A method for implanting a first and second lead parallel to each other and parallel to the midline of a patient's spinal cord, comprising:
    providing an introducer, wherein the introducer has a first lumen and a second lumen, the second lumen being collapsible and expandable and being collapsed as the introducer is inserted into a patient;
    inserting a guidewire in proximity to the patient's spinal cord;
    inserting the guidewire into a lumen of a dilator;
    inserting the dilator into the first lumen of the introducer;
    advancing the dilator and introducer over the guidewire wherein the introducer is inserted such that a distal portion of the first lumen is parallel to the midline of the spinal cord;
    expanding the second lumen such that a distal portion of the lumen resides on an opposing side of the midline relative to the first lumen;
    inserting the first lead into the first lumen of the of the introducer;
    inserting the second lead into the second lumen; and
    withdrawing the introducer and leaving distal portions of the first and second leads parallel to each other and parallel to the midline of a patient's spinal cord.

9. The method of claim 8, wherein the dilator comprises a needle tip configured to puncture the patient's skin, and wherein the method further comprises gaining access to the patient's epidural space by percutaneously inserting the needle tip of the dilator into the patient until the tip reaches the epidural space.

10. A method for implanting a first and second lead parallel to each other and parallel to the midline of a patient's spinal cord, comprising:

inserting an introducer in proximity to the patient's spinal cord, wherein the introducer has a main body defining a main lumen, a first side sheath defining a first side lumen, and a second side sheath defining a second side lumen, the first and second side sheaths being attached to generally opposing sides of the main body and being collapsible and expandable and being collapsed as the introducer is inserted, wherein the introducer is inserted such that that a distal portion of the main lumen is parallel to the midline of the spinal cord;

expanding the first side sheath such that a distal portion of the first lumen resides on a side of the midline of the patient's spinal cord;

inserting the first lead into the first side lumen;

expanding the second side sheath such that a distal portion of the second side lumen resides on a side of the midline of the patient's spinal cord opposing the side on which the first side lumen resides;

inserting the second lead into the second side lumen; and withdrawing the introducer and leaving distal portions of the first and second leads parallel to each other and parallel to the midline of a patient's spinal cord.

11. The method of claim 10, further comprising inserting a dilator into the main lumen of the introducer, and advancing the dilator over a guidewire, wherein inserting the introducer comprises advancing the dilator over the guidewire.

12. The method of claim 11, wherein the dilator comprises a needle tip configured to puncture the patient's skin, and wherein the method further comprises gaining access to the patient's epidural space by percutaneously inserting the needle tip of the dilator into the patient until the tip reaches the epidural space.

* * * * *